(12) United States Patent
Lin et al.

(10) Patent No.: US 12,232,808 B2
(45) Date of Patent: Feb. 25, 2025

(54) OPTOTYPE CALIBRATION METHOD

(71) Applicant: Crystalvue Medical Corporation, Taoyuan (TW)

(72) Inventors: Chun Nan Lin, Bade (TW); Kun Cheng Hsieh, New Taipei (TW)

(73) Assignee: Crystalvue Medical Corporation, Taoyuan (TW)

( * ) Notice: Subject to any disclaimer, the term of this patent is extended or adjusted under 35 U.S.C. 154(b) by 604 days.

(21) Appl. No.: 17/686,087

(22) Filed: Mar. 3, 2022

(65) Prior Publication Data
US 2022/0395173 A1 Dec. 15, 2022

(30) Foreign Application Priority Data
Jun. 10, 2021 (TW) .................. 110121233

(51) Int. Cl.
*A61B 3/032* (2006.01)
*A61B 3/00* (2006.01)
(52) U.S. Cl.
CPC ............ *A61B 3/032* (2013.01); *A61B 3/0008* (2013.01)

(58) Field of Classification Search
CPC .............................. A61B 3/032; A61B 3/0008
See application file for complete search history.

(56) References Cited

U.S. PATENT DOCUMENTS

2012/0249951 A1* 10/2012 Hirayama .............. A61B 3/032
351/201

* cited by examiner

*Primary Examiner* — James C. Jones
(74) *Attorney, Agent, or Firm* — Patterson + Sheridan, LLP

(57) ABSTRACT

An optotype calibration method is disclosed. The optotype calibration method includes steps of: (a) when a first optotype and a second optotype located outside an observable area, moving the observable area from an original position until the first optotype or the second optotype appears in the observable area; (b) adjusting a focus mechanism to make the first optotype and the second optotype close to each other; (c) moving the observable area back to the original position; and (d) repeating the steps (a)~(c) until the first optotype and the second optotype align with each other.

10 Claims, 3 Drawing Sheets

S10

S12

S14

S16

S18

OPTOTYPE CALIBRATION METHOD

BACKGROUND OF THE INVENTION

Field of the Invention

The invention relates to an optotype; in particular, to an optotype calibration method.

Description of the Prior Art

In general, when the eyes of a person to be tested undergoing vision testing have nearsightedness/farsightedness, it is easy to cause the upper and lower optotypes used for vision testing to separate in the horizontal direction. In other words, if the eyes of the person to be tested have a high degree of nearsightedness/farsightedness and their pupil size is small, the upper and lower optotypes separated in the horizontal direction are likely to be out of the observable area of the eyes of the person to be tested. Therefore, the current vision testing device urgently needs to calibrate the upper and lower optotypes to improve the accuracy of vision testing.

SUMMARY OF THE INVENTION

Therefore, the invention provides an optotype calibration method to solve the above-mentioned problems of the prior arts.

A preferred embodiment of the invention is an optotype calibration method. In this embodiment, the optotype calibration method includes steps of: (a) when a first optotype and a second optotype are located outside an observable area, moving the observable area from an original position until the first optotype or the second optotype appears in the observable area; (b) adjusting a focus mechanism to make the first optotype and the second optotype close to each other; (c) moving the observable area back to the original position; and (d) repeating the steps (a)~(c) until the first optotype and the second optotype are aligned with each other.

In an embodiment, the step (a) is to move the observable area in a first direction and the step (c) is to move the observable area in a second direction, wherein the first direction and the second direction are opposite to each other.

In an embodiment, the steps (a) and (c) move the observable area by moving a scanning head.

In an embodiment, the step (a) further includes: determining whether the first optotype or the second optotype appears in the observable area in an image processing way.

In an embodiment, the step (b) further includes: adjusting the focus mechanism through a software-controlled motor to make the first optotype and the second optotype close to each other.

In an embodiment, the optotype calibration method is applied to a vision testing device.

In an embodiment, in the vision testing device, an illumination light emitted by a light source module sequentially passes through an optotype optical module, a first reflector, a second reflector and an eyepiece and enters a pupil of an eye to be tested through an illumination light path.

In an embodiment, an image light generated by the illumination light reflected by the eye to be tested sequentially passes through the eyepiece, the second mirror and an optical lens module and enters a camera model through an image light path.

In an embodiment, the vision testing device further includes a control module. The control module is electrically connected to the optotype optical module and the camera module to control operations of the optotype optical module and the camera module respectively.

In an embodiment, the vision testing device further includes a control motor. The control motor is electrically connected between the control module and the optotype optical module. The control module controls an operation of the optotype optical module through the control motor.

Compared to the prior art, the optotype calibration method of the invention can be applied to a vision testing device to calibrate the positions of the upper and lower optotypes. Even if the eyes of the person to be tested undergoing vision testing have a high degree of nearsightedness/farsightedness and their pupil size is small, after the upper and lower optotypes are calibrated by the optotype calibration method of the invention, the upper and lower optotypes can be aligned with each other without deviating from the observable area of the eyes of the person to be tested can effectively improve the accuracy of vision testing.

The advantage and spirit of the invention may be understood by the following detailed descriptions together with the appended drawings.

BRIEF DESCRIPTION OF THE APPENDED DRAWINGS

FIG. 3 shows a schematic diagram of the vision testing device that the optotype calibration method of the invention is applied to.

DETAILED DESCRIPTION OF THE INVENTION

Figure 1:
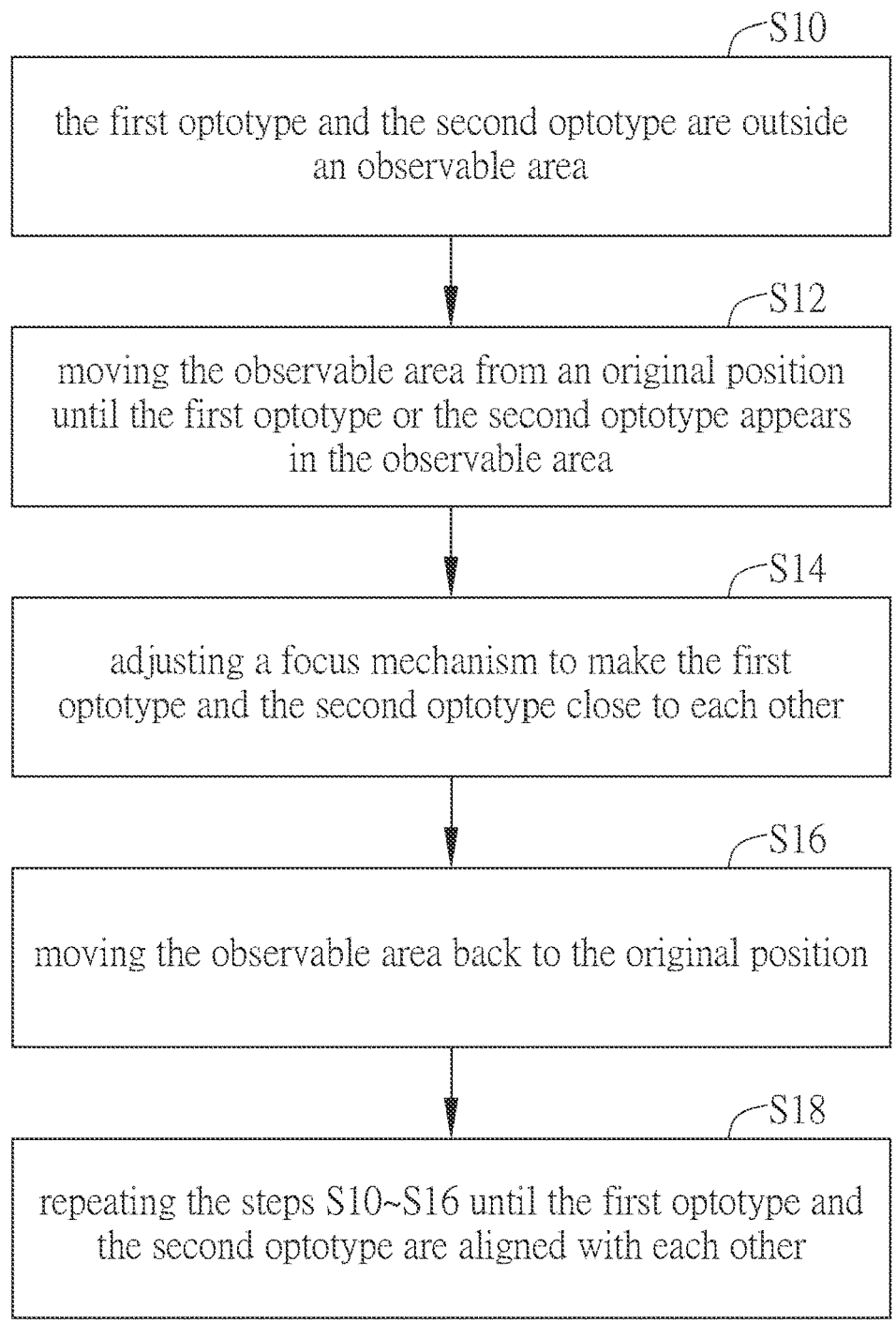
FIG. 1 shows a flowchart of the optotype calibration method in a preferred embodiment of the invention.

Exemplary embodiments of the invention are referenced in detail now, and examples of the exemplary embodiments are illustrated in the drawings. Further, the same or similar reference numerals of the components/components in the drawings and the detailed description of the invention are used on behalf of the same or similar parts.

A specific embodiment of the invention is an optotype calibration method. In this embodiment, the optotype calibration method can be applied to a vision testing device to calibrate the positions of the upper and lower optotypes for the vision testing of the person to be tested, so that the upper and lower optotypes are aligned with each other and do not deviate from the observable area of the eyes of the person to be tested.

Please refer to FIG. 1. FIG. 1 shows a flowchart of the optotype calibration method in this embodiment. As shown in FIG. 1, the optotype calibration method includes following steps S10~S18:

Step S10: the first optotype and the second optotype are outside an observable area;

Step S12: moving the observable area from an original position until the first optotype or the second optotype appears in the observable area;

Step S14: adjusting a focus mechanism to make the first optotype and the second optotype close to each other;

Step S16: moving the observable area back to the original position; and

Step S18: repeating the steps S10~S16 until the first optotype and the second optotype are aligned with each other.

In practical applications, the first optotype and the second optotype can be upper and lower optotypes, and there are no specific restrictions on the shape and size. The steps S12 and S16 can move the observable area by moving a scanning head, but not limited to this.

In an embodiment, the step S12 is to move the observable area in a first direction and the step S16 is to move the observable area in a second direction, and the first direction and the second direction are opposite to each other. For example, the first direction is to the left and the second direction is to the right, but not limited to this.

In another embodiment, the step S12 can determine whether the first optotype or the second optotype appears in the observable area in an image processing way, but not limited to this.

In another embodiment, the step S14 can adjust the focusing mechanism through a software-controlled motor to make the first optotype and the second optotype close to each other, but not limited to this.

Figure 2:
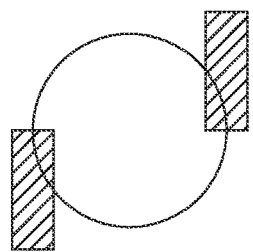
FIG. 2 shows a schematic diagram corresponding to the steps S10~S18 in FIG. 1.
Figure 2:
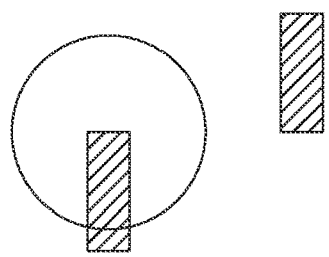
Figure 2:
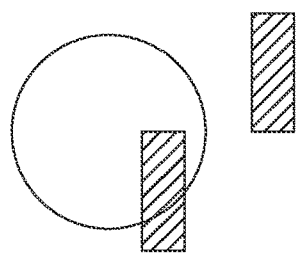
Figure 2:
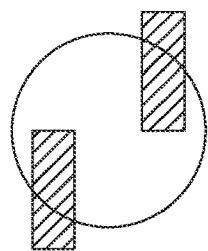
Figure 2:
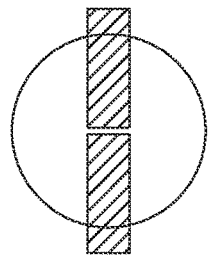

As for the schematic diagrams of the above-mentioned steps S10~S18, please refer to FIG. 2, which will not be repeated here.

Figure 3:
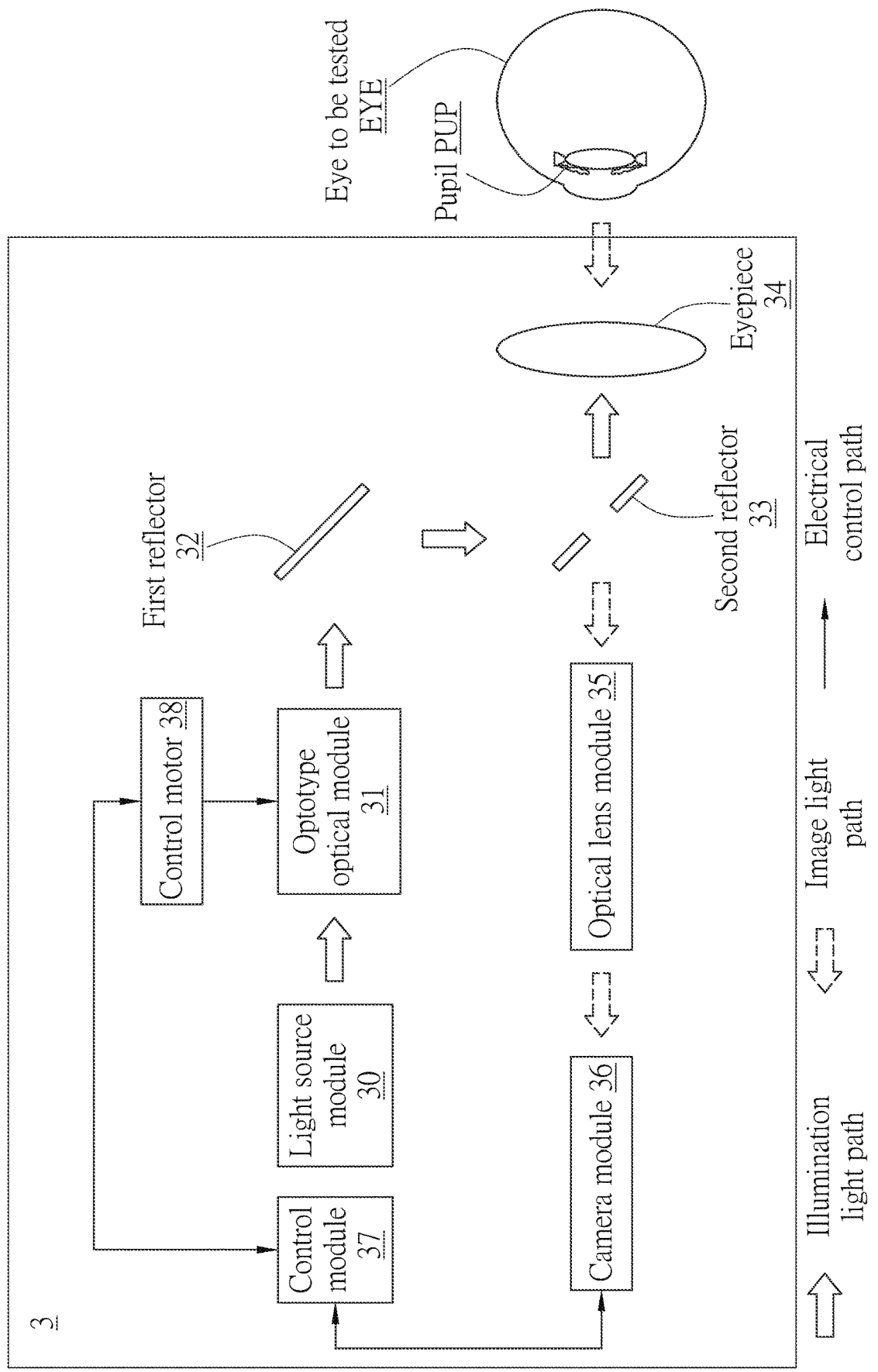

Next, please refer to FIG. 3. FIG. 3 shows a schematic diagram of the vision testing device that the optotype calibration method of the invention is applied to.

As shown in FIG. 3, the vision testing device 3 includes a light source module 30, an optotype optical module 31, a first reflector 32, a second reflector 33, an eyepiece 34, an optical lens module 35, a camera module 36, a control module 37 and a control motor 38.

The camera module 36 and the control module 37 are electrically connected to each other. The control motor 38 and the control module 37 are electrically connected to each other. The optotype optical module 31 and the control motor 38 are electrically connected to each other. The control module 37 controls the operation of the camera module 36 and controls the operation of the optotype optical module 31 through the control motor 38.

In the vision testing device 3, an illumination light emitted by the light source module 30 sequentially passes through the optotype optical module 31, the first reflector 32, the second reflector 33 and the eyepiece 34 and enters a pupil PUP of an eye to be tested EYE through an illumination light Path. An image light generated by the illumination light reflected by the pupil PUP of the eye to be tested EYE sequentially passes through the eyepiece 34, the second reflector 33 and the optical lens module 35 and enters the camera module 36 through the image light path, so that the camera module 36 can capture images.

Compared to the prior art, the optotype calibration method of the invention can be applied to a vision testing device to calibrate the positions of the upper and lower optotypes. Even if the eyes of the person to be tested undergoing vision testing have a high degree of nearsightedness/farsightedness and their pupil size is small, after the upper and lower optotypes are calibrated by the optotype calibration method of the invention, the upper and lower optotypes can be aligned with each other without deviating from the observable area of the eyes of the person to be tested can effectively improve the accuracy of vision testing.

With the example and explanations above, the features and spirits of the invention will be hopefully well described.

Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optotype calibration method, comprising steps of:
   (a) when a first optotype and a second optotype are located outside an observable area, moving the observable area from an original position until the first optotype or the second optotype appears in the observable area;
   (b) adjusting a focus mechanism to make the first optotype and the second optotype close to each other;
   (c) moving the observable area back to the original position; and
   (d) repeating the steps (a)~(c) until the first optotype and the second optotype are aligned with each other.

2. The optotype calibration method of claim 1, wherein the step (a) is to move the observable area in a first direction and the step (c) is to move the observable area in a second direction; the first direction and the second direction are opposite to each other.

3. The optotype calibration method of claim 1, wherein the steps (a) and (c) move the observable area by moving a scanning head.

4. The optotype calibration method of claim 1, wherein the step (a) further comprises:
   determining whether the first optotype or the second optotype appears in the observable area in an image processing way.

5. The optotype calibration method of claim 1, wherein the step (b) further comprises:
   adjusting the focus mechanism through a software-controlled motor to make the first optotype and the second optotype close to each other.

6. The optotype calibration method of claim 1, wherein the optotype calibration method is applied to a vision testing device.

7. The optotype calibration method of claim 6, wherein in the vision testing device, an illumination light emitted by a light source module sequentially passes through an optotype optical module, a first mirror, a second mirror and an eyepiece and enters a pupil of an eye to be tested through an illumination light path.

8. The optotype calibration method of claim 7, wherein an image light generated by the illumination light reflected by the eye to be tested sequentially passes through the eyepiece, the second mirror and an optical lens module and enters a camera model through an image light path.

9. The optotype calibration method of claim 8, wherein the vision testing device further comprises a control module, and the control module is electrically connected to the optotype optical module and the camera module to control operations of the optotype optical module and the camera module respectively.

10. The optotype calibration method of claim 9, wherein the vision testing device further comprises a control motor, and the control motor is electrically connected between the control module and the optotype optical module, the control module controls an operation of the optotype optical module through the control motor.

* * * * *